United States Patent [19]

Palson et al.

[11] Patent Number: 5,119,806
[45] Date of Patent: * Jun. 9, 1992

[54] INHALATION DEVICE

[75] Inventors: Richard C. J. Palson, Medfield; John C. Armstrong, Milton, both of Mass.; Alfred G. Childers, Cary, N.C.

[73] Assignee: Glaxo Inc., Research Triangle Park, N.C.

[*] Notice: The portion of the term of this patent subsequent to Jul. 16, 2008 has been disclaimed.

[21] Appl. No.: 452,718

[22] Filed: Dec. 14, 1989

Related U.S. Application Data

[63] Continuation-in-part of Ser. No. 183,499, May 3, 1988, Pat. No. 5,031,610, which is a continuation-in-part of Ser. No. 48,808, May 12, 1987, abandoned.

[51] Int. Cl.$^5$ ............................................. A61M 11/00
[52] U.S. Cl. ............................ 128/200.14; 128/200.23
[58] Field of Search ....................... 128/200.14, 200.23

[56] References Cited

U.S. PATENT DOCUMENTS

| | | |
|---|---|---|
| 3,157,179 | 11/1964 | Paullus et al. |
| 3,456,645 | 7/1969 | Brock |
| 3,456,646 | 7/1969 | Phillips et al. |
| 3,598,294 | 8/1971 | Hedrick et al. ............... 222/402.2 |
| 3,636,949 | 1/1972 | Kropp |
| 3,789,343 | 2/1974 | Armstrong et al. |
| 3,814,297 | 6/1974 | Warren |
| 3,826,413 | 7/1974 | Warren ..................... 222/402.13 |
| 4,414,972 | 11/1983 | Young et al. ................ 128/200.23 |
| 4,592,348 | 6/1986 | Waters, IV et al. ......... 128/200.23 |
| 4,648,393 | 3/1987 | Landis ........................ 128/200.23 |
| 4,664,107 | 5/1987 | Wass ........................... 128/200.23 |
| 4,803,978 | 2/1989 | Johnson et al. ............. 128/200.23 |

FOREIGN PATENT DOCUMENTS 3040641 5/1982 Fed. Rep. of Germany.
8501880 5/1985 PCT Int'l Appl..

Primary Examiner—Edgar S. Burr
Assistant Examiner—Aaron J. Lewis
Attorney, Agent, or Firm—Darby & Darby

[57] ABSTRACT

A device for dispensing an aerosol from an aerosol module containing aerosol under pressure wherein there is a cocking device for readying it for release of the pressurized aerosol, a sear for retaining the cocking device in a non-operative position following readying and a vane operable by inhalation on the part of a user to disable the sear to thus release the cocking device to effect expulsion of aerosol from the aerosol module. The cocking device further includes a recocking member that is automatically releasable at the end of the discharge cycle to permit a valve in the module to return to its disabled position and ensure complete refilling of a metering chamber.

5 Claims, 11 Drawing Sheets

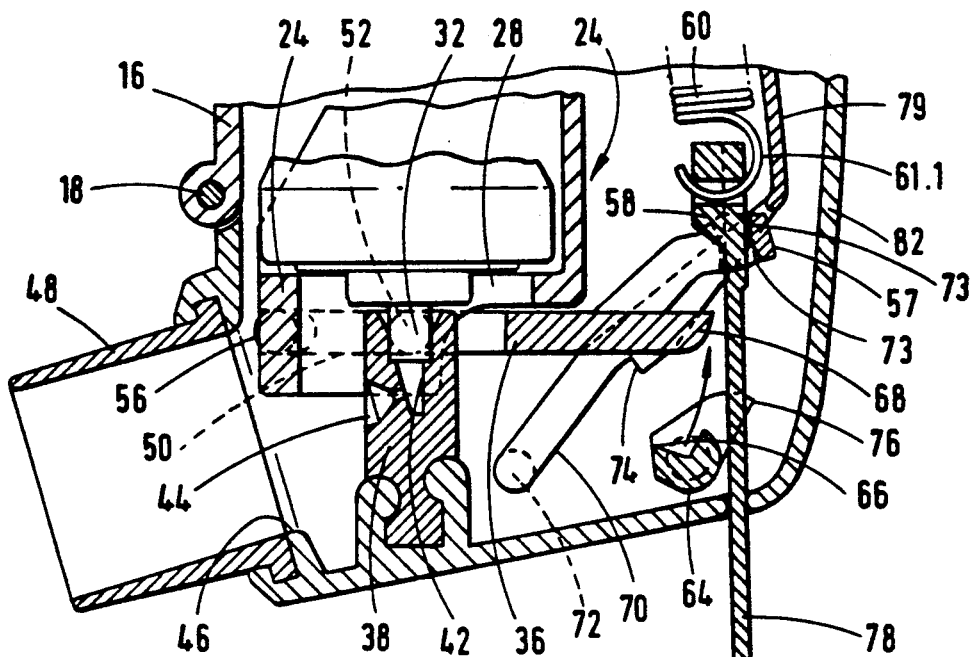
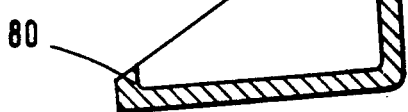
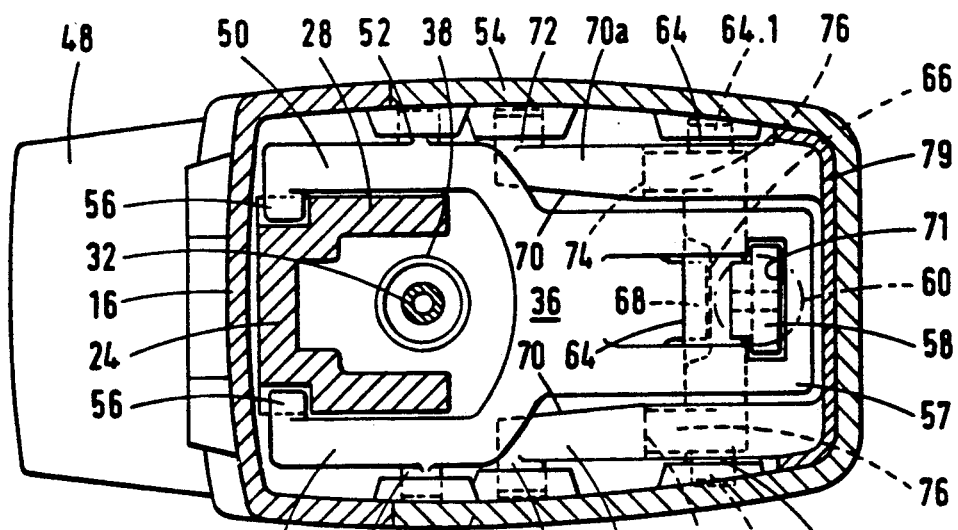

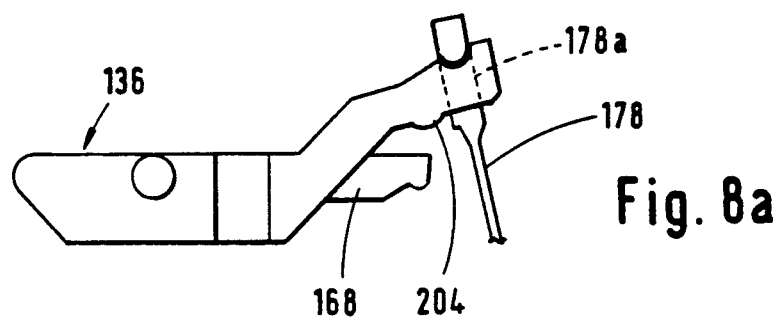
Fig. 8a
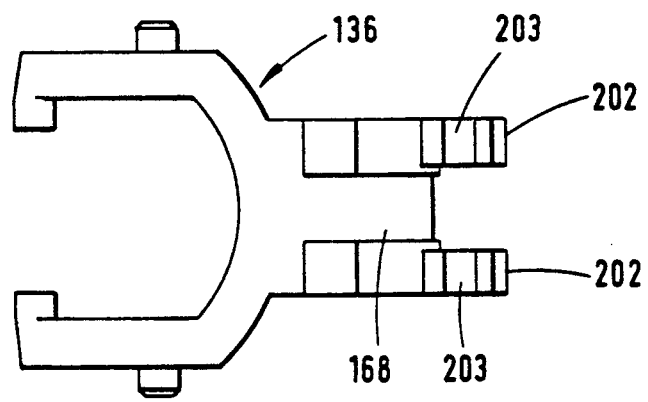
Fig. 8b
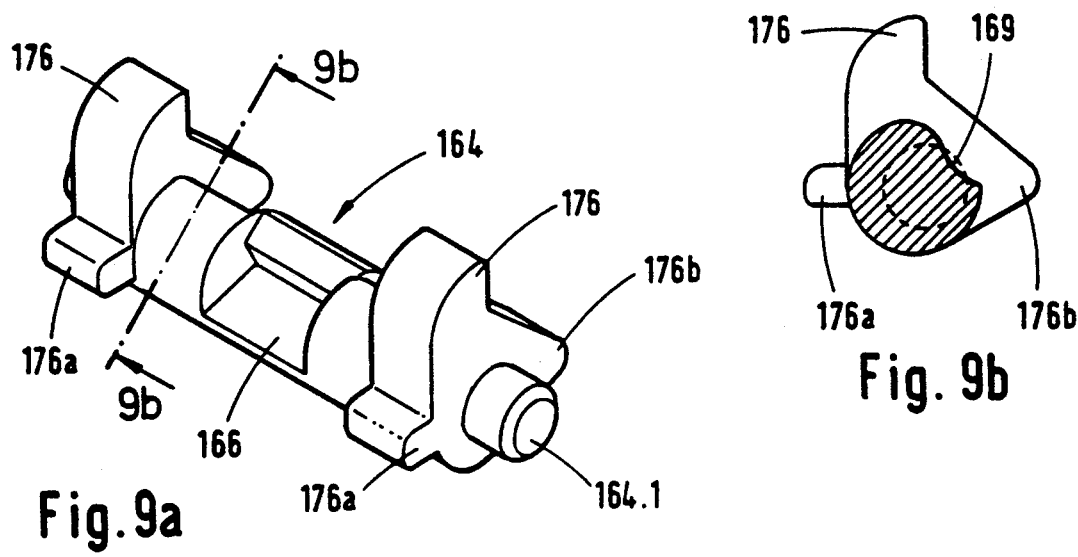
Fig. 9a
Fig. 9b

INHALATION DEVICE

RELATED APPLICATIONS

This application is a Continuation-in-Part of previously filed application Ser. No. 183,499 filed May 3, 1988 now U.S. Pat. No. 5,031,610, entitled INHALATION DEVICE, which was a Continuation-in-Part of our previously filed application Ser. No. 48,808, filed May 12, 1987, also entitled INHALATION DEVICE, now abandoned.

BACKGROUND OF THE INVENTION

There are a number of devices for dispensing aerosols for nasal and/or oral inhalation. Such devices are now quite well known for administering medicaments to patients suffering from bronchial conditions such as, for example, bronchial asthma. The most significant problem associated with such aerosols has been the difficulty for many patients to coordinate the release of the medicament with the initiation of the inspiratory effort. Many people, for example, elderly patients and children, find this synchronization difficult. These problems are alleviated with the breath-actuated devices such as the ones disclosed in U.S. Pat. Nos. 3,639,949; 3,789,843; 3,826,413; and W085/01880. Sometimes these devices are also referred to as inhalation-oriented aerosols or, more simply, "demand valves". Simply, these devices eliminate the need for manual coordination by actuating automatically when the patient inhales with his lips in contact with the mouthpiece. Only light negative pressure is required to trip a simple mechanism which actuates the metering valve. The device must then be reset before the metering valve may discharge again. The instant application is concerned with a breath-actuated device of this type, but embodies improvements over the devices in the aforesaid patents in that it is structured to minimize the occasions of accidental discharge and, yet, discharge can be effected with minimum effort.

A long-standing problem with breath-actuated dispenser development has been the incompatibility between the strong spring required to overcome the internal aerosol valve spring for effecting discharge, and the light pressure available to impaired individuals to trigger the device. The juncture between the two aforementioned elements in the past has been so tenuous that even the surface coefficient of friction of materials had to be considered. By the introduction of an intermediate sear element and other improvements to accomplish greater mechanical advantage, this invention achieves a positive yet sensitive latching and the degree of integrity required in medical dispensing devices.

Additionally, some types of discharge valve constructions require that the aerosol container be in the vertical position to assure complete filling of the medicament metering chamber. In many of these devices recharging is delayed and, as a result, the can or container may be in other than a vertical position when recharged with the end result that less than a full dosage refills the metering chamber. The present invention allows automatic recharging at the end of the discharge cycle thereby ensuring that a full dosage enters the metering chamber.

A further problem encountered during discharge is due to the drag of the recocking mechanism which may interfere with the amount of medicament discharged during the discharge cycle. Accordingly, the present invention also contemplates the use of a retractable cocking strap to eliminate such frictional problems.

SUMMARY OF THE INVENTION

As herein illustrated, the device is structured for use with an aerosol module and comprises a housing, a cradle disposed in the housing for receiving an aerosol module provided with a valve or discharge stem. The stem is movable with respect to the module from a disabling position to prevent discharge to an enabling position to permit discharge, the cradle being movable relative to the housing, a discharge nozzle member mounted in the housing in alignment with the discharge stem with which the discharge stem is engaged such that movement of the cradle relative to the nozzle effects relative movement between the module and the stem, a lever mounted in the housing operable to effect movement of the cradle relative to the nozzle member in a direction to enable the stem, to thus discharge a needed amount of aerosol formulation, spring means connected to the lever biasing the lever in a direction to enable the stem and means for constraining movement of said lever in said direction to enable the stem, comprising a sear disposed adjacent the distal end of the lever with which the distal end of the lever is engaged, a latch engaged with the sear holding the sear in the lever engaged position such that the stem is disabled, and means for disengaging the latch from the sear such as to permit the spring to move the lever to a position to enable the discharge stem. The lever is coupled to the cradle such that pivotal movement of the lever will on the one hand move the cradle in a direction to disable the stem and on the other hand move the cradle in a direction to enable the stem. There is cocking means coupled to the lever operable to move the lever in opposition to the spring means to a position to disable the stem and there is means for enabling the cocking means and for disabling the cocking means. The latch is pivotally supported at one end and has at its other end an arm accessible through an opening in the housing for manual displacement in a direction to disengage the latch from the sear in the event that the user has difficulty in initiating release by inspirational effort. The housing has an opening adjacent the nozzle member through which the aerosol ejected by engaging the valve can be projected and there is a closure member adapted to close the discharge opening and means connecting the closure member to the spring to hold the latter distended and the lever in a position such that the stem is disabled.

Further features and advantages of the invention appear from the ensuing description of several illustrated embodiments. In particular, means are described by which the discharge stem can return to its disabled position immediately, or almost immediately, after the device has fired. Further, the device preferably comprises a cocking strap, and means may be provided whereby the cocking strap remains stationary while the device is being fired.

The invention will now be described with reference to the accompanying drawings, wherein:

FIG. 3 is a vertical section of the device of FIG. 1 showing the components in their operated or discharged position;

FIG. 4 is a transverse section taken on the line 4—4 of FIG. 1;

FIGS. 8a and 8b are respectively an elevation and a plan view of the yoke used in the second embodiment. FIG. 8a showing also a portion of a strap attached thereto;

FIGS. 9a and 9b are respectively a perspective view and a cross-section taken along line 9b—9b of FIG. 9a of the sear used in the second embodiment;

Figure 12A:
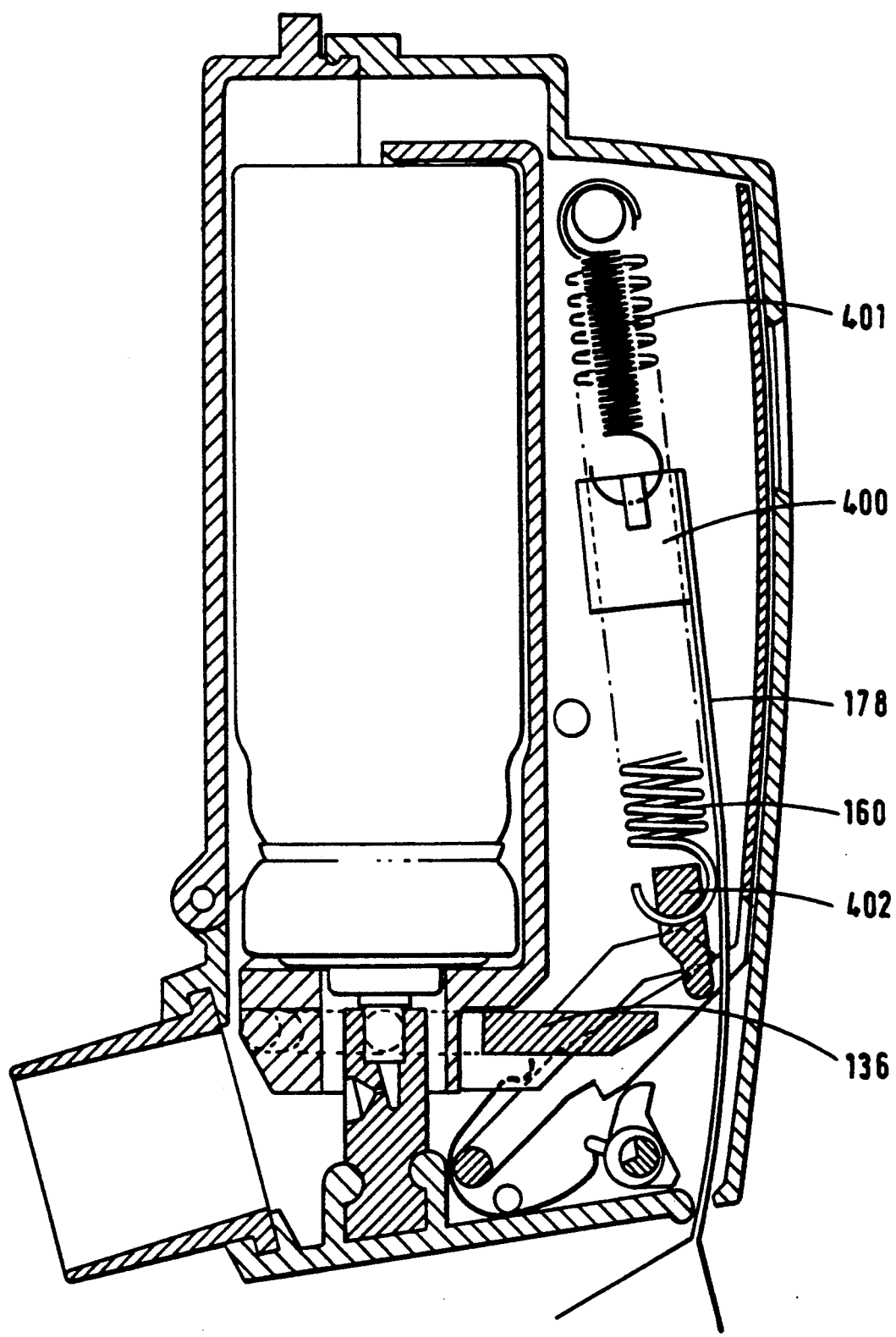
Figure 12B:
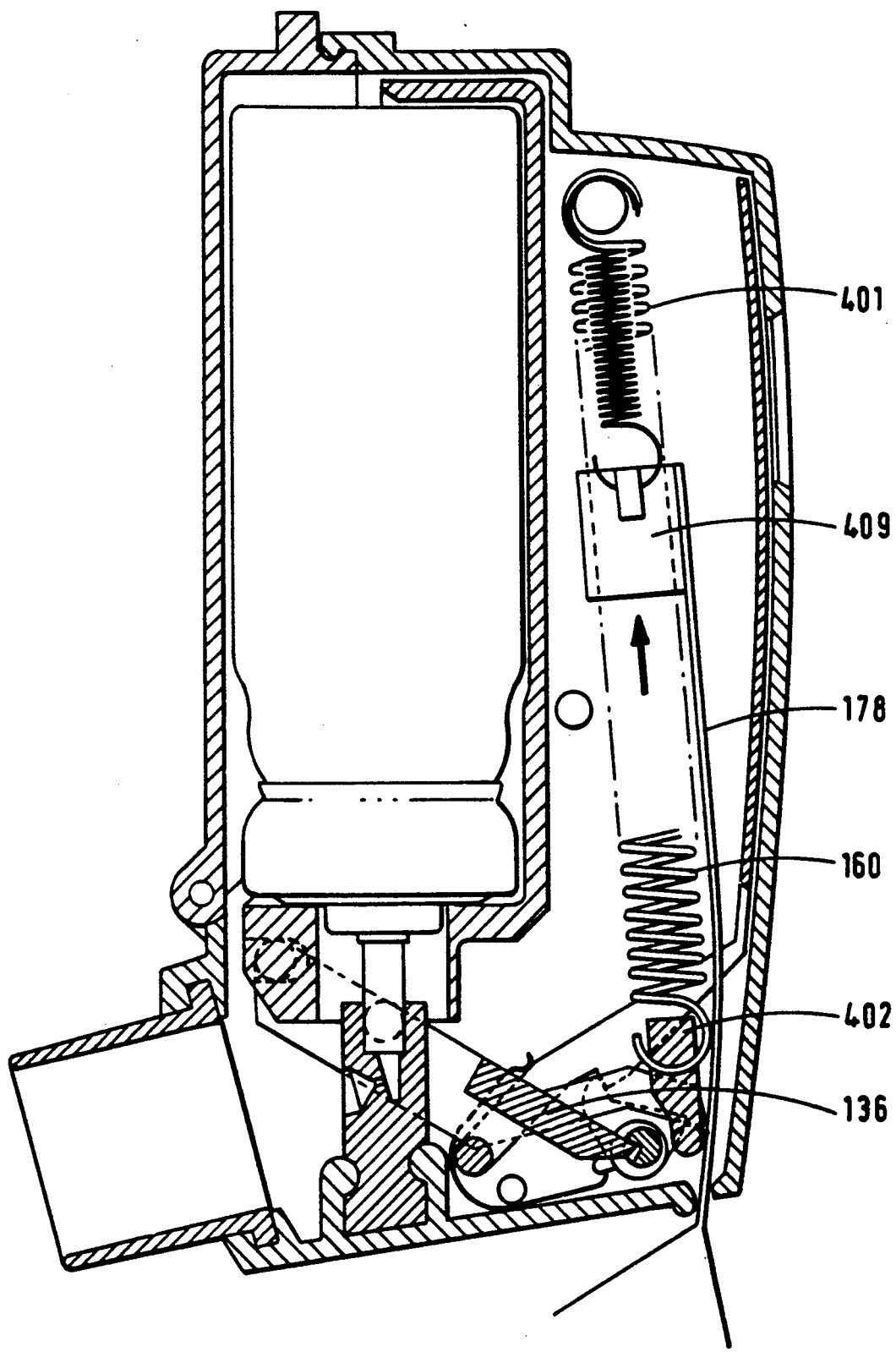
Figure 13A:
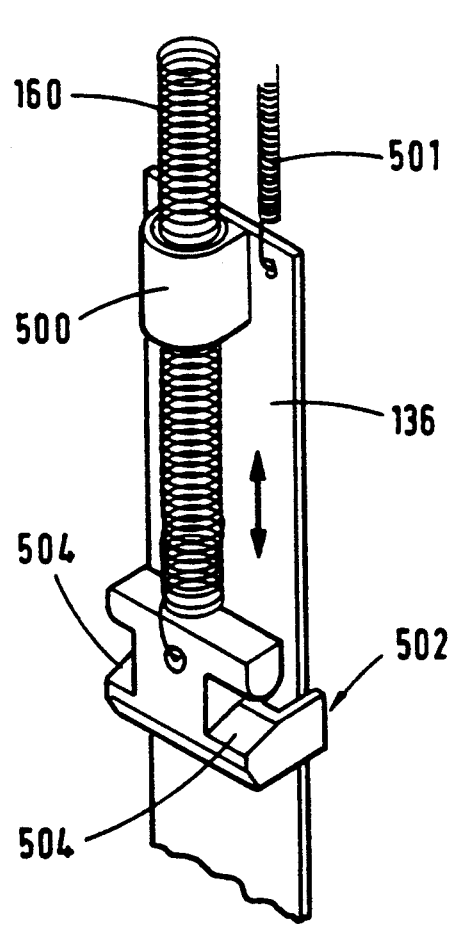
Figure 13B:
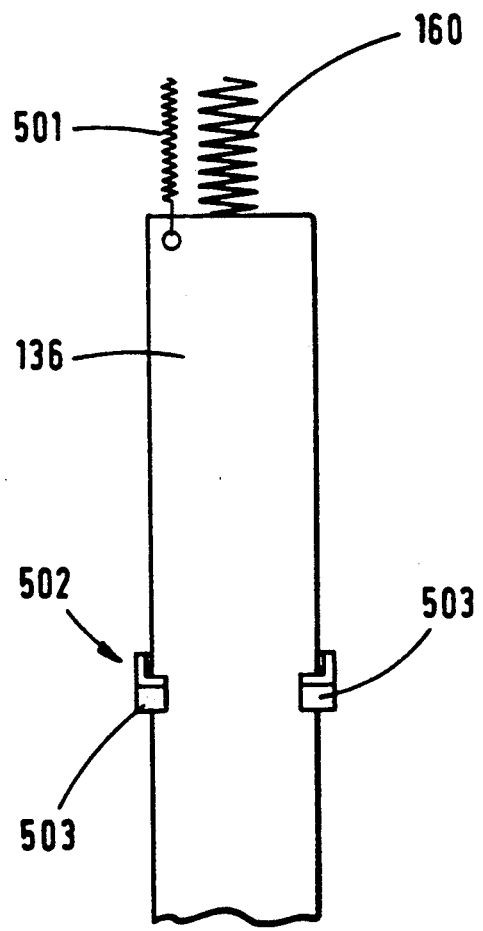

FIGS. 12a and 12b are respective vertical sectional views through a further embodiment, with a strap which remains stationary during firing; FIG. 12a shows the elements in the cocked position and FIG. 12b shows the elements in the discharged position; and FIGS. 13a and 13b are respectively a perspective view and a rear elevation of the further modification of FIGS. 12a and 12b which provides a strap which is both releasably connected to the yoke and which remains stationary during firing.

Referring to FIGS. 1 to 4 of the drawings, the device shown therein comprises a housing 10 defining chambers 12 and 14. A closure member 16 is hinged at one end by a pin 18 to one side of the chamber 12, the closure being provided at its opposite end with a latch element 20 interengageable with a latch element 22 on the housing.

A cradle member 24 is mounted within the chamber 12 for vertical movement therein. The cradle 24 has semicircular side wall 26 of a dimension and configuration corresponding substantially to the length and cross section of the aerosol module A to be disposed in the chamber and a bottom wall 28 containing a circular opening 30 for supporting the module in an inverted position within the chamber with its stem 32 extending through the bottom wall 28 into the chamber below the cradle. Desirably, the cradle 24 has at its upper end a capping element 34 for engagement with the bottom of the module to hold the module firmly engaged with the bottom 28. The cradle 24 is movable vertically within the housing 10 and there is means in the form of a yoke-shaped lever 36 operative in one position to hold the cradle 24 in an elevated position and in another position to hold it in a depressed position.

In that portion of the housing 10 below the cradle 24, there is mounted in a fixed position a nozzle member 38 containing an opening 40. The nozzle member 38 is disposed in alignment with the stem 32 for receiving the stem 32. The opening 40 is connected by a passage 42 to a discharge opening 44, the axis of which is concentrically centered with respect to an opening 46 formed in the lower part of the chamber 12 within which there is disposed an annular mouthpiece 48. As thus arranged, discharge from the aerosol module, as will appear hereinafter, is directed by the nozzle member 38 through the mouthpiece 48. Since the stem 32 remains stationary in the nozzle member 38 during operation, the desired dispersal pattern is maintained at all times.

Discharge of aerosol from the module is effected by moving the cradle 24 downwardly relative to the nozzle member 38 to displace the stem 32 in the module. The aerosol module has a metering valve therein so that displacement of the stem 32 dispenses a dose of the material contained by the module through the nozzle element and directs it through the mouthpiece 48. After the dose has been dispensed no further material emerges from the stem until the stem has been first returned to its disabled position and then again put in its enabled position.

As herein illustrated, the yoke-shaped lever 36, FIG. 4, is provided with transversely spaced arms 50 each provided with a respective trunion 52 pivotally supported in the opposite side walls 54 of the housing for pivotal movement about a horizontal axis intermediate its opposite ends. At one end, the arms 50 of the yoke are pivotally connected by respective trunions 56 with the lower end of the cradle. At the opposite end, the lever 36 is connected by an arm 57 and coupling element 58 to the lower end 61.1 of a tension spring 60 mounted within the chamber 14. The arm 57 contains an opening 71 having oppositely diverging sides 73 through which the coupling element 58 extends. The upper end 61.2 of the spring 60 is connected to a pin 62 fixed between the walls of the chamber 14.

Within the lower end of the chamber 14, there is mounted a sear 64 which is rotatable about a horizontal axis parallel to the axis of rotation of the lever 36. The sear 64 extends across the chamber 14 from one side wall 54 to the other and is mounted for pivotal movement about the aforesaid horizontal axis by trunions 64.1 pivotally supported in the side walls 54. The sear 64 is provided in a central region thereof with a notch 66 of generally right angular section for engagement with the distal end portion 68 of the lever 36. The distal end position 68 and the notch 66 are sized and positioned so that the end portion 68 engages notch 66 immediately adjacent the pivot axis to minimize the forces on the lever 36 when the elements are engaged. The sear 64 is rotatable about its axis between one position in which it holds the distal end portion 68 of the lever 36 depressed (FIG. 1), in which position the opposite end of the lever holds the cradle 24 elevated and, hence, the stem 32 fully extended, and another position to release the distal end portion 68 of the lever 36 and allow the lever 36 to be elevated by the spring to a horizontal position (FIG. 3), such as to lower the cradle to a position to force the stem 32 into the module to cause aerosol discharge.

A latch member 70 having a pair of arms 70a is pivotally mounted at 72 to the side walls 54 for movement about a horizontal axis parallel to the axis of the sear. The latch 70 is provided adjacent its axially opposite ends with a pair of abutments 74 each of which is interengageable with a respective arm 76 integral with the sear.

Figure 1:
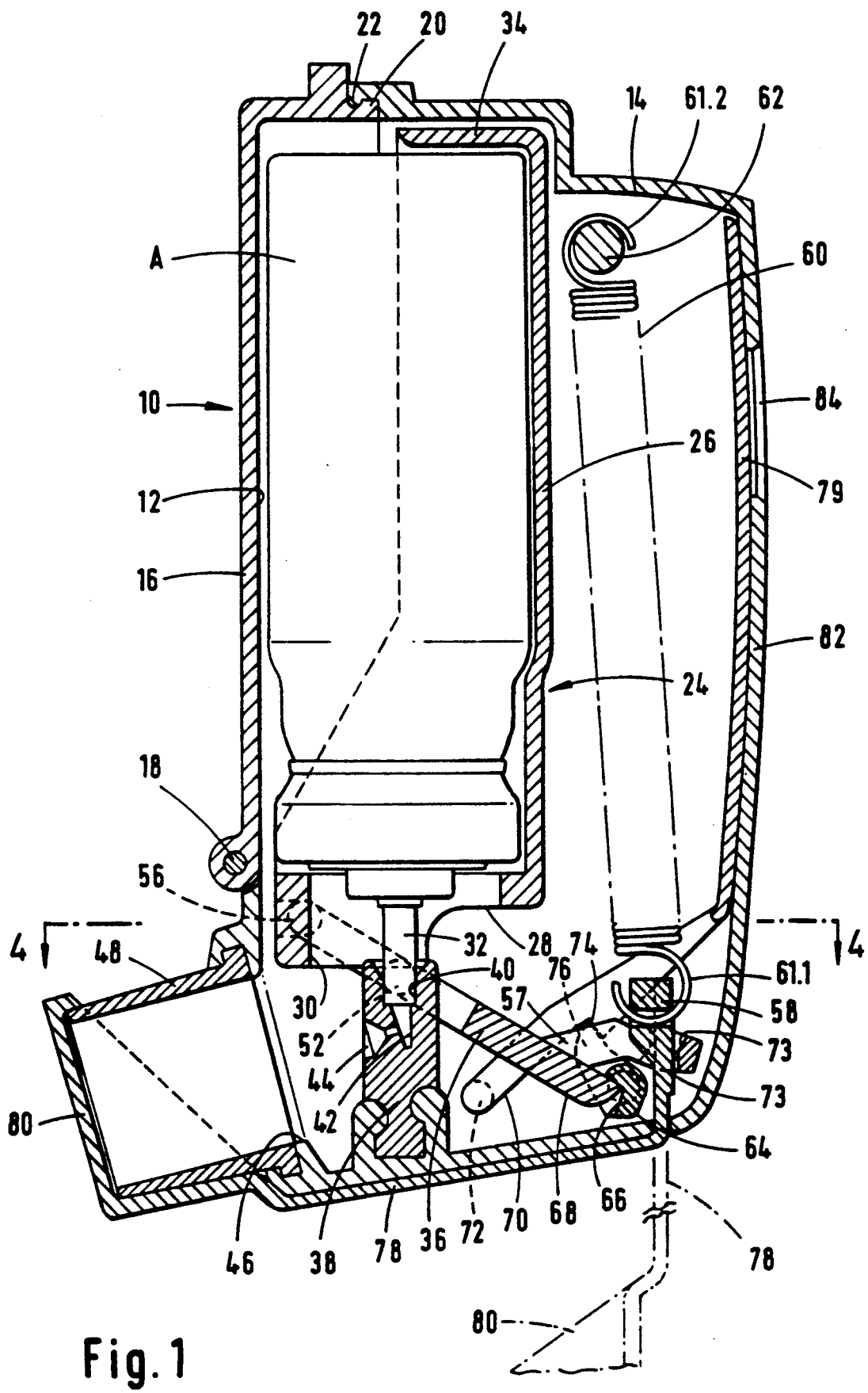
FIG. 1 is a vertical section of a first embodiment of the device, showing the components thereof in their inoperative position.

In the inoperative position of the device, FIG. 1, the end 68 of the lever 36 is held in the depressed position by a cocking strap 78, one end of which is connected to the coupling 58 to which the spring 60 is attached and the other end of which has connected to it a cap 80 which fits over the end of the mouthpiece 48. When the cap 80 is fitted to the mouthpiece, the strap by way of the coupling 58 holds the spring 60 extended and the lever 36 in the depressed position with its distal end engaged with the sear 64. In this position, the abutments 74 of the latch member 70 prevent rotation of the sear 64. In practice, with the elements in the position shown in FIG. 1, there is a slight spacing between the facing surfaces of abutments 74 and arms 76. This permits the latch member to easily fall back into the position shown in FIG. 1 if it is accidently displaced prior to use. If such spacing was not provided, the latch member could seat on the edge of the sear if the latch member is accidently displaced thereby allowing immediate discharge of the medicament when cap 80 is taken off the mouthpiece, as noted more fully below.

The latch member 70 has connected to its distal end an air vane 79 which, in the position of the latch as shown in FIG. 1, parallels the wall 82 of the chamber 14 and in this parallel position, covers an opening 84 in the wall. In the non-operative position of the device, the cap 80 is engaged with the mouthpiece 48, the air vane is engaged with the wall 82 so as to cover the opening 84 and the linkage is held in the position shown in FIG. 1 by the spring 60 so that the stem 32 is fully extended, that is, in the shut off position.

Figure 2:
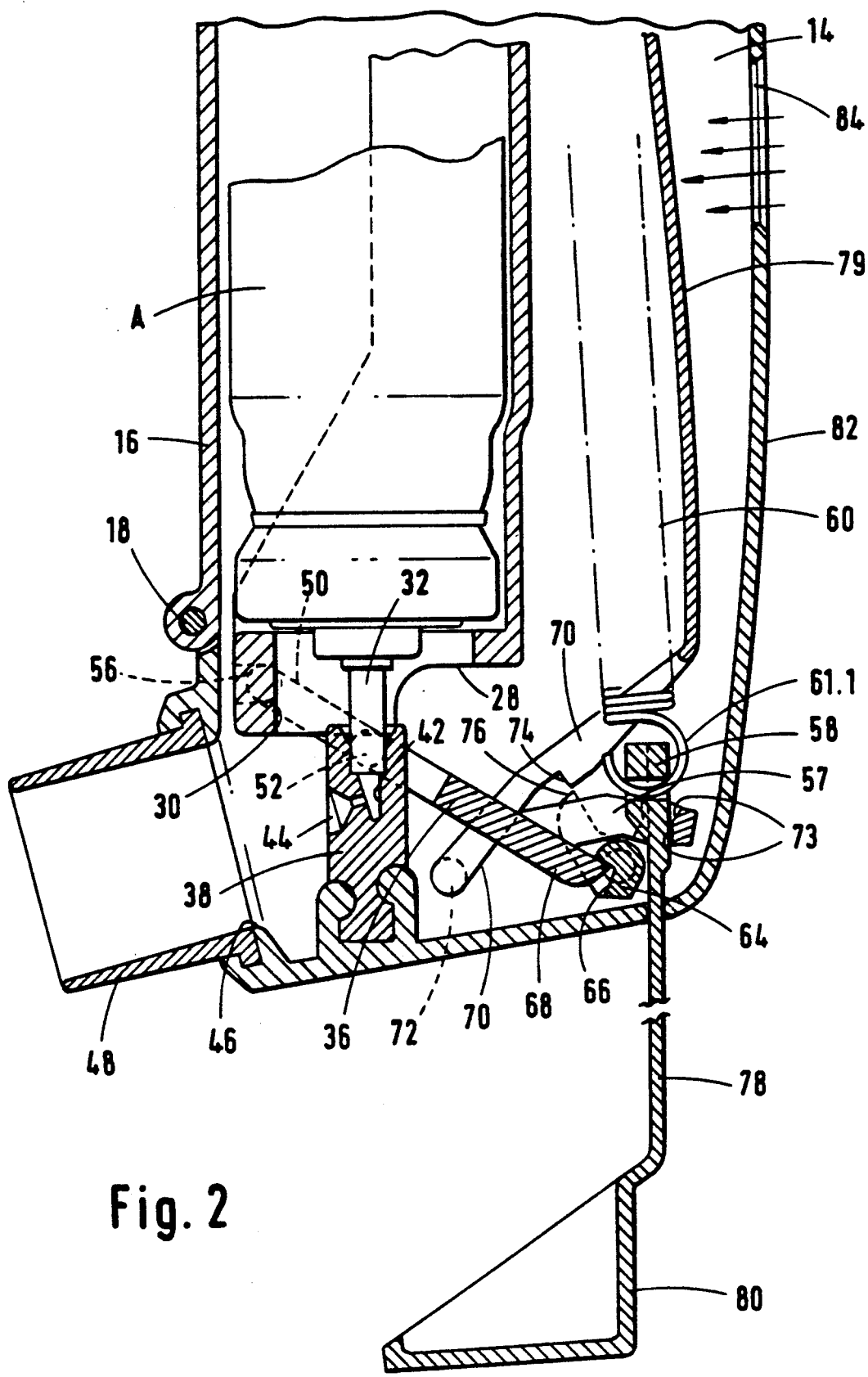
FIG. 2 is a vertical section of the device of FIG. 1 showing the components thereof at the instant of initiation of operation of the device.

To ready the device for use, the cap 80 is disengaged from the mouthpiece 48, FIG. 2. Disengagement of the cap allows the strap 78 to free the distal end of the arm 57 so that the distal end of the lever 36 is held depressed only by virtue of the fact that the lever 36 cannot move without its distal end position 68 rotating the sear, and the sear cannot rotate because of the engagement of the arms 76 with the abutments 74 of the latch member 70. (That is, with cap 80 free, the sear 64 is rotated counterclockwise to close the gap between the facing surfaces of the sear and the latch member.) With the cap 80 removed, the device is ready for use. When the user inhales through the mouthpiece 48, thus lowering the pressure in the chamber 14, the air vane 79 swings from its position of engagement with the wall 82 toward the left, as illustrated in FIG. 3. Movement of the air vane 79 to the left disengages the abutments 74 of the latch member 70 from the arm 76, thus freeing the sear 64 to rotate. The spring 60 is thus able to pull the right hand end of the lever 36 upwardly. Since the lever 36 is mounted for pivotal movement with respect to the housing by the trunions 52 this causes the left hand end of the lever 36 to move downwardly carrying the cradle 24 with it. Downward movement of the cradle 24 displaces the stem 32 into the module which effects discharge of aerosol from the module through the nozzle and mouthpiece. When the aspiration is discontinued, the air vane assumes its closed position under the influence of gravity.

After inhalation the user grips the cap 80 and pulls downwardly on it against the force exerted via the strap 78 by the spring 60. The user is then able to reengage the cap 80 on the mouthpiece 48. The device is thus restored to the position shown in FIG. 1. It will be observed that this involved, inter alia, the restoration of the lever 36, sear 64 and the latch member 70 to the positions of FIG. 1, and the way in which this occurs will now be described briefly.

As the cap and strap are pulled down the lever 36 pivots about the trunions 52 in a clockwise direction as viewed in FIGS. 1 to 3, and a point is reached where the distal end portion 68 comes into contact with the notch 66 in the central region of the sear 64. As downward movement of the cap and strap continues the engagement between the distal end portion 68 and the notch 66 causes the sear 64 to pivot in a counterclockwise direction. In the course of this counterclockwise pivoting movement the arms 76 strike the undersides of the respective latch member arms 70a and the latch member 70 is thus caused to pivot counterclockwise through a small angle to allow the arms 76 to pass. Once the arms 76 are past the respective abutments 74 the latch member 70 is free to fall into the position shown in FIG. 1 under the influence of gravity, with the arms 76 each engaged behind a respective abutment 74. At this point the configuration shown in FIG. 1 is attained.

The embodiment shown in FIGS. 5 to 9 is similar in many respects to the embodiment shown in FIGS. 1 to 4, and will therefore not be described in detail. Elements in the embodiment of FIGS. 5 to 9 which correspond broadly to elements in the embodiment of FIGS. 1 to 4 are denoted by the same reference numerals but with the addition of 100. Attention will now be drawn to the more significant of the aspects in which the embodiment of FIGS. 5 to 9 differs from the embodiment of FIGS. 1 to 4.

Figure 5:
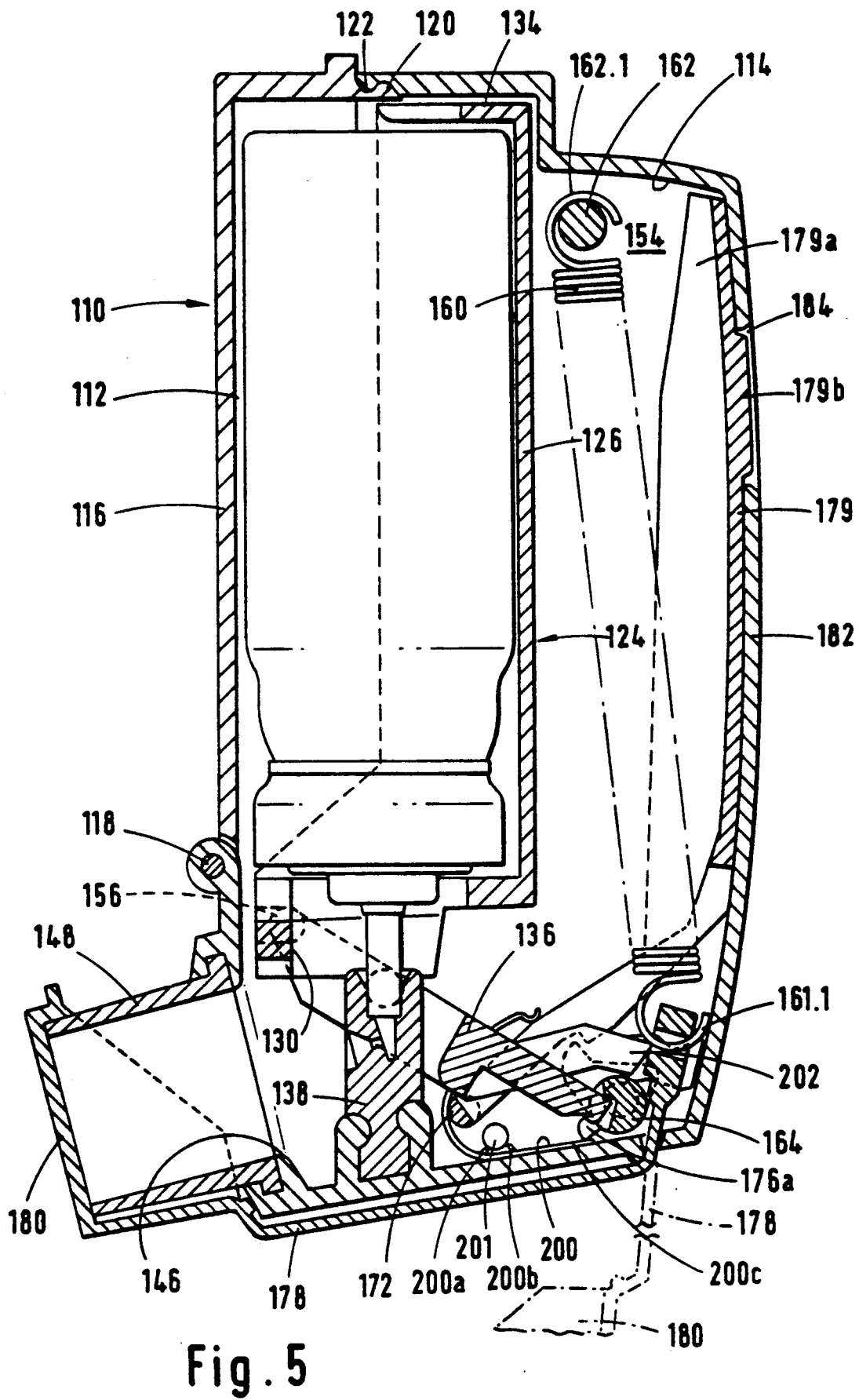
FIGS. 5 to 7 are views corresponding to FIGS. 1 to 3 respectively of a second embodiment.

Attention is directed firstly to the construction of the sear 164. For convenience this is shown on an enlarged scale in perspective in FIGS. 9a and 9b. It will be seen that each of the arms 176 has a protrusion 176a which extends approximately radially in a direction generally at right angles to the direction in which the main body of the arm 176 extends. As can be seen in FIG. 5, when the device is its inoperative position one of these protrusions 176a bears against a flat spring 200 which is of generally U-shape and which is secured intermediate its ends to the bottom of the housing. The spring 200 extends about a pin 201 extending laterally from one of the side walls 154 of the housing. The spring includes upwardly bent portions 200a and 200b located on opposite sides of the pin which serve to position the spring relative to the pin. The extension 200c of the spring is inclined upwardly and is depressed by the protrusion 176a when the elements are in the position shown in FIG. 5. Accordingly, the flat spring biases the sear in the clockwise direction. No second strip spring need be provided on the other side of the device, and the other protrusion 176a is therefore, strictly speaking, unnecessary. The protrusions 176a serve firstly to prevent the sear from rotating too far counterclockwise as viewed in FIGS. 5 to 7. In the absence of the protrusions the sear might rotate so far that the notch 166 would not be in a position to be engaged by the distal end portion 168 of the lever 136 during the procedure of restoring the device to its initial inoperative condition after inhalation (i.e. restoring it to the condition shown in FIG. 5). The presence of the protrusions 176a and the clockwise bias of the spring 200 acting on the protrusion 176a ensures that the notch 166 is in the correct position after inhalation for engagement by the distal end portion 168.

The protrusion 176a which engages the spring 200 has a light force exerted thereon by the spring, and this provides an additional impetus to the sear to ensure its clockwise rotation when inhalation takes place, over and above the force exerted on the notch 166 by the distal end portion 168 of the lever 136.

It will also be seen from FIGS. 9a and 9b, that on the opposite side of the arm 176 to the protrusion 176a is a further protrusion 176b. As can be appreciated by considering, for example FIG. 7, the protrusions 176b prevent excessive rotation of the sear in a clockwise direction by abutting the bottom wall of the housing.

One further aspect of the sear which should be noted is that the regions of the sear immediately on either side of the notch 166 are provided with recesses 169. During the initial stage of returning the device after inhalation to the state of FIG. 5 rotation of the sear in a counterclockwise direction is accomplished by engagement between the distal end portion 168 of the lever 136 and the notch 166. However, the final portion of this counterclockwise rotation is accomplished by engagement between cam surfaces 204 on the lever 136 and the recesses 169. At this point it may be convenient to note that the yoke 136 differs somewhat from the yoke 36 used in the first embodiment. In particular, the arm 57 is absent, so that there extends rearwardly from the main portion of the lever 136 a pair of arms 202 which are not connected at their rearward ends. The upper portion of the strap has a section of reduced width and increased thickness 178a between the arms 202, and sections of full width and increased section immediately above and below the arms. The section above the arms is convex and is received in a pair of concave recesses 203, one formed in each of the arms 202.

Figure 6:
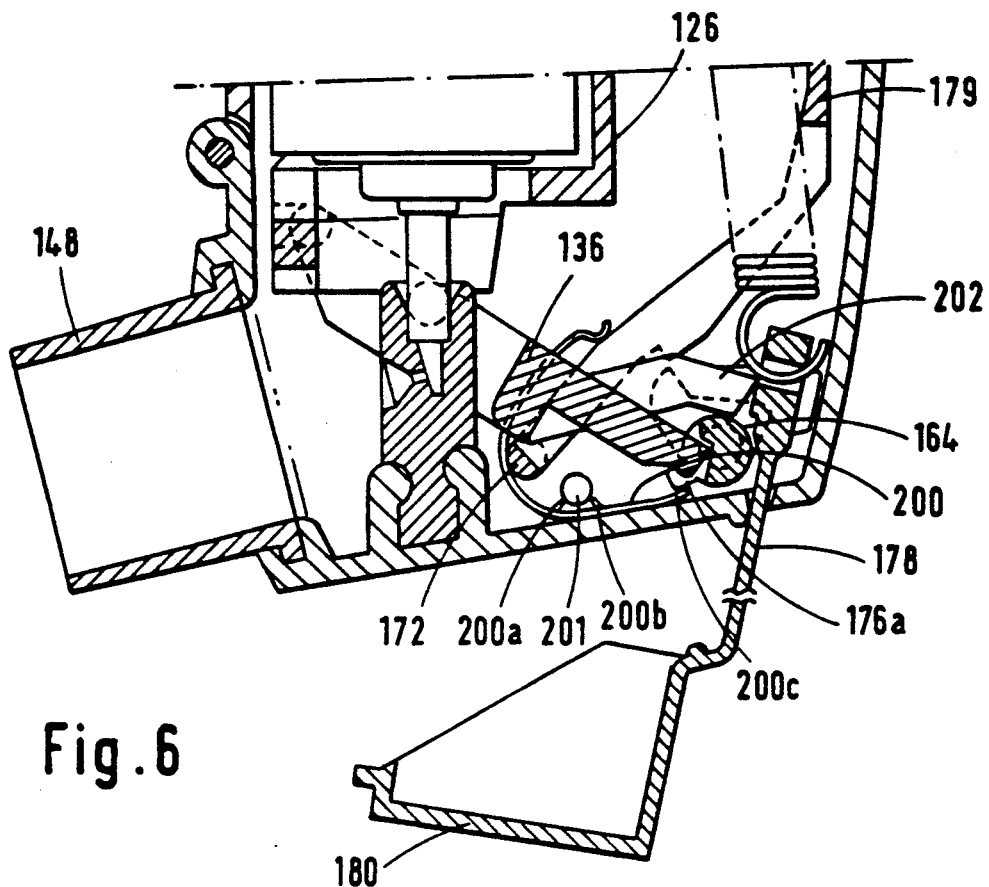
Figure 7:
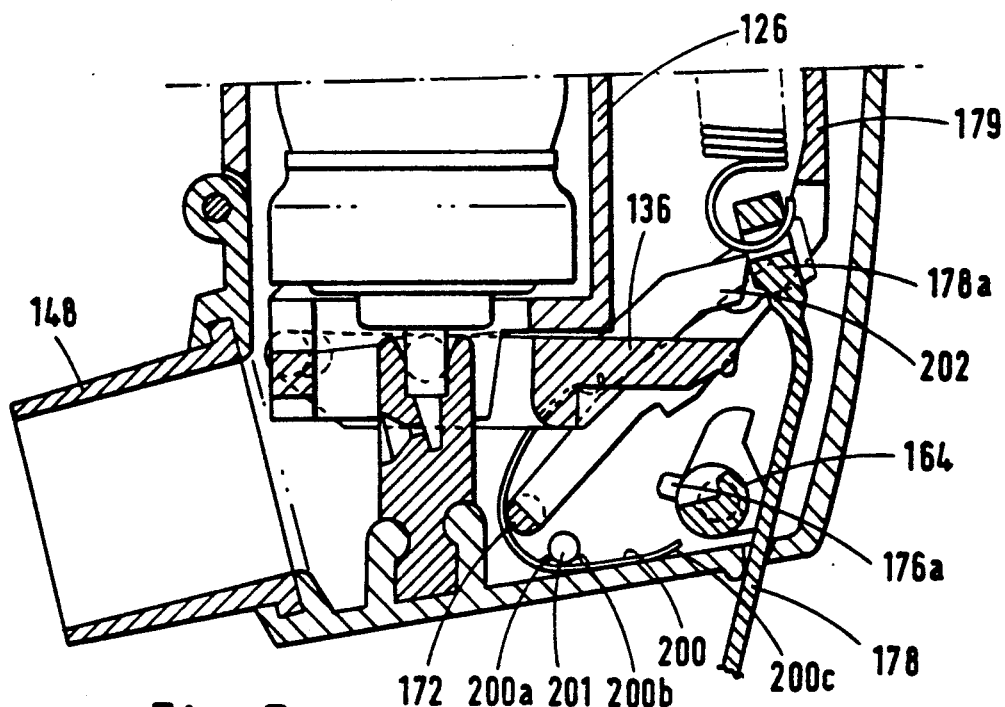

The U-shaped spring 200 serves a purpose in addition to exerting a force on one of the protrusions 176a. As can be seen in FIGS. 5 to 7 the upper portion of the spring bears on one of the arms 70a of the latch member 70. This helps to ensure that after the cap 180 has been removed from the nozzle 48, as indicated in FIG. 6, the latch member 70 cannot become accidentally disengaged from the arms 76, and that disengagement will only take place when the user inhales. The presence of the spring 200 means that a slight additional force has to be exerted through inhalation in order to disengage the latch member from the arms 76, but this additional force is slight, provided the spring 200 is chosen to be appropriately weak. Furthermore, the effect of the spring 200 in requiring an additional force is more than counterbalanced by an improvement in the design of the air vane of the embodiment of FIGS. 5 to 9, over and above the air vane used in the embodiment of FIGS. 1 to 4. As can be seen in FIG. 5, the air vane 179 is provided with side walls 179a which extend forwardly from the main portion of the air vane and approximately perpendicular thereto. The side walls are each close to a respective side wall 154, and their presence helps to ensure that the suction force produced when a patient inhales is highly effective in producing a force on the air vane. The main portion of the air vane 179 has a button 179b which, in the position shown in FIG. 5, is received in the opening 184. The main purpose of this is to provide a button which is clearly identifiable to a user as being such. It should be mentioned at this point that if a user desires to do so he can, instead of operating the device automatically by inhalation, operate it by pressing the button 179b and thereby causing the air vane 179 to move inwardly as it would have done had the patient caused it to move by inhalation.

Figure 10A:
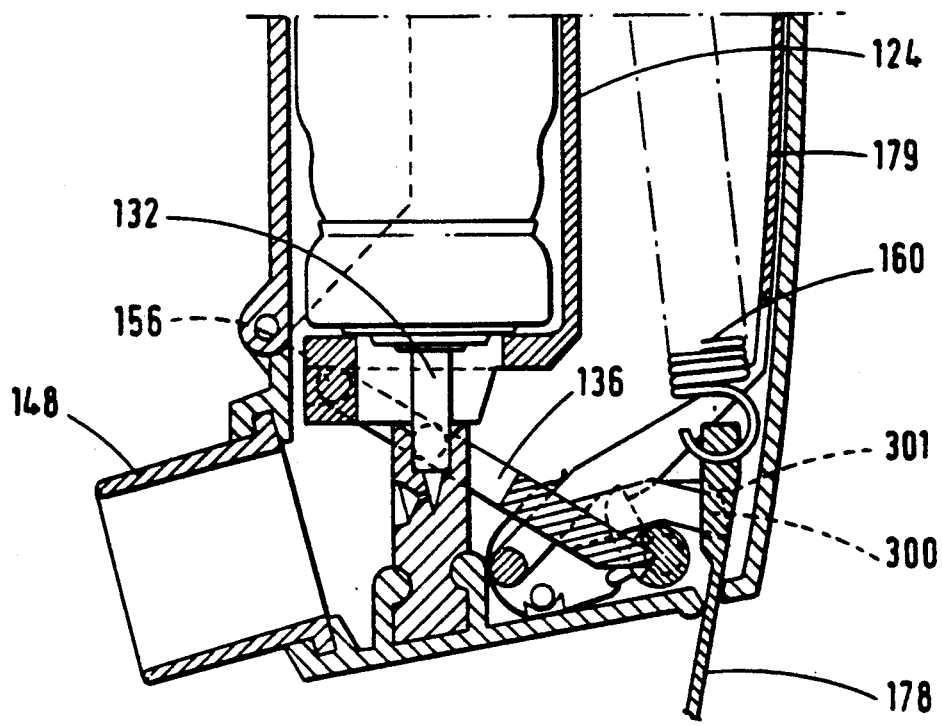
FIGS. 10a to 10d are vertical sections which show, in part, successive stages in the operation of a modified embodiment in which the strap is releasably connected to the yoke.
Figure 10B:
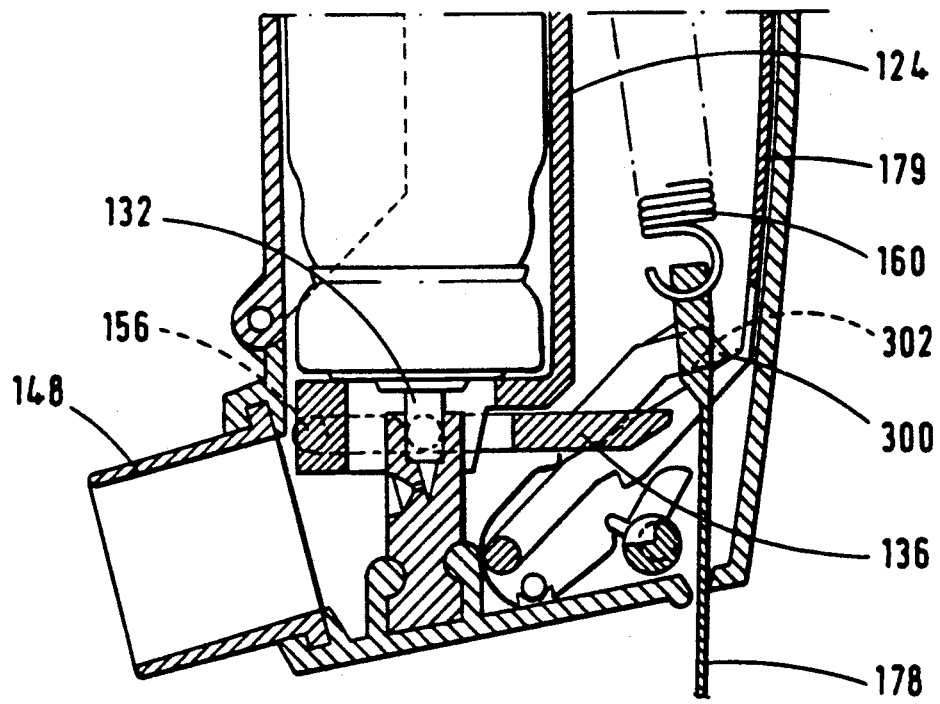
Figure 10C:
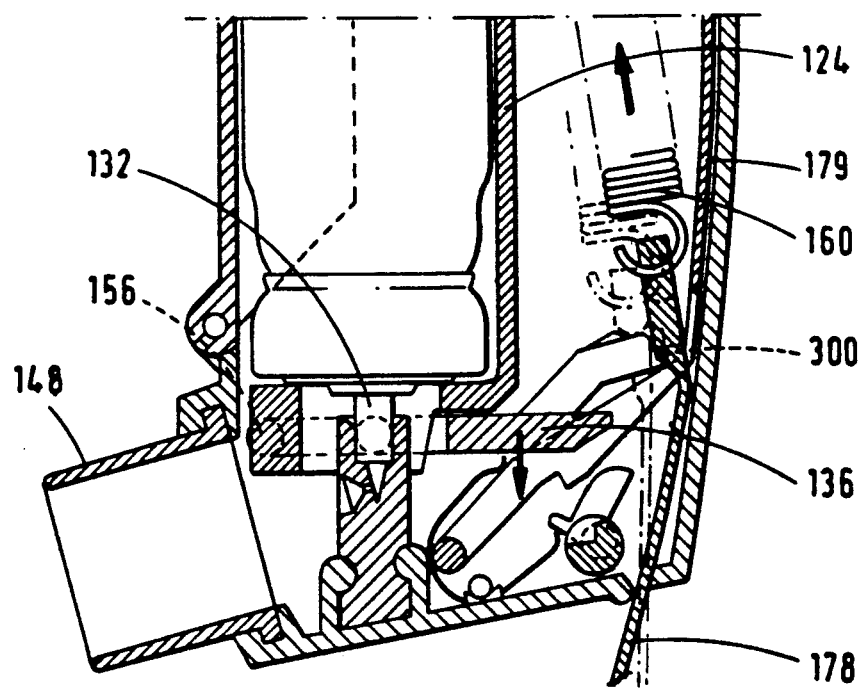
Figure 10D:
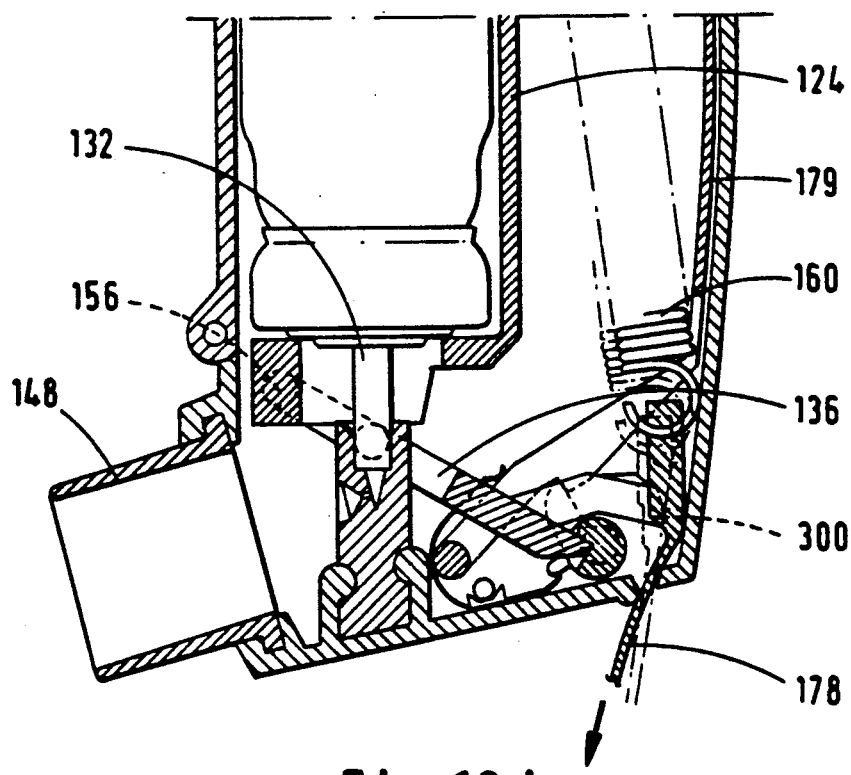

FIGS. 10a to 10d show a modified form of device in successive positions of operation which ensures automatic and full refilling of the valve metering chamber. FIG. 10a shows the device in the cocked position ready for firing. FIG. 10b shows the device immediately after firing. FIG. 10c shows the device at an instant in time slightly later than FIG. 10b. FIG. 10d shows the device towards the end of the cocking process.

The device shown in FIGS. 10a to 10d is substantially the same as that shown in FIGS. 7 to 9, except as regards the manner in which the force from the spring 160 is transmitted to the lever or yoke 136. Accordingly, in FIGS. 10a to 10d the same reference numerals are used therein as are used in FIGS. 5 to 9 for corresponding components, with reference numerals of 300 and above being used for features which significantly differ.

Figure 11:
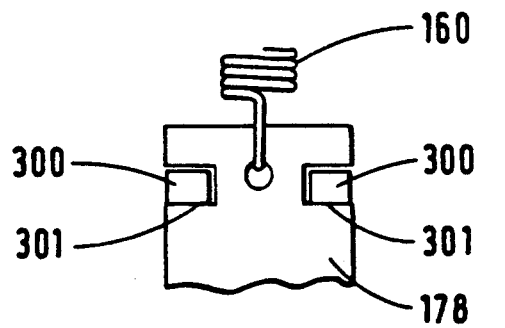
FIG. 11 is a detail view showing the interconnection of the yoke and strap of FIGS. 10a to 10d.

Referring first to FIG. 10a, taken in conjunction with FIG. 11, it will be seen that the rear end of the lever or yoke 136 has a pair of end portions 300, one on each side thereof, each of which engages in a respective opening 301 which extends inwardly from a respective edge of the strap 178. As will become apparent from the following description, the end portions 300, are held releasably in the openings 301.

When the user inhales through the mouthpiece 148 the air vane 179 moves forward and, as explained in connection with the preceding embodiment, this permits the yoke 133 to pivot in an anticlockwise direction under the force of the spring 160. As also explained in connection with the preceding embodiment, this pulls down the cradle 124 which carries the aerosol module, thus producing relative inward movement between the body of the aerosol module and its stem 132. A dose is thereby discharged from the stem through the mouthpiece 158.

The spring 160 continues to exert an upward force on the strap 178, and hence on the rear end portions 300 of the yoke As can be seen from FIG. 10b, the interengaging surfaces 302 of the strap 178 and end portions 300 are not precisely at right angles to the direction of pull of the spring, with the result that there is a component of force on the strap tending to cause it to move rightwardly with respect to the end portions 300, as viewed in FIG. 10b. This has the effect, which is shown in FIG. 10c, of causing the strap to slide rightwardly off the end portions and then travel upwardly with respect to the end portions. Once this has occurred there is no longer any upwardly directed force on the rear end of the yoke 136. There is thus no longer any force tending to pull the cradle 124 downwardly. The stem 132 is biased outwardly with respect to the remainder of the aerosol module by an internal spring, which is not shown and which is conventional. This internal spring is relatively weak, far weaker than the spring 160. However, when the spring 160 no longer exerts a force on the yoke and hence on the cradle, the internal spring is sufficient to push the aerosol module upwardly with respect to the stem, carrying the cradle 124 with it. Thus, the metering chamber in the aerosol module valve is able immediately to completely refill with a dose from the reservoir of material present within the aerosol module. Moreover, except for the position of the strap 178, the elements will assume the position shown in FIG. 10d.

As noted above, the metering chamber will only refill completely if the aerosol module is in a substantially vertical position during refill. Thus, in the case of the embodiments of FIGS. 10a to 10d and FIG. 11 it is virtually certain that the device will still be in this position for at least a short period after firing, and at any rate for long enough for the metering chamber to completely refill.

The device may be recocked by pulling downwardly on the strap 178. Since the slot through which the strap exits is slightly forward of the end portions 300, the strap exerts a force to the left as taken in FIG. 10c. As the strap moves downwardly, it slides past the end portions 300 until the openings 301 are reached, whereupon the strap moves slightly toward the left and captures the end portions 300 in the respective openings 301. Thus, all of the elements will be in the position shown in FIG. 10d.

FIGS. 12a and 12b show a further embodiment. The numbering convention used in FIGS. 12a and 12b is the same as that used in FIGS. 10a to 10d and FIG. 11, except that here additional features are denoted by reference numerals of 400 and above.

During firing of the device the strap moves rapidly upwards. Accordingly, it is possible that the strap may be subject to interference as a result of contact between it and adjacent parts of the device. This can have an adverse metering chamber. Furthermore, the movement of the strap and the cap which is attached to it, closely adjacent to, or even in contact with, the user's face, may be objectionable from the point of view of the user. The design of the embodiment of FIGS. 12a and 12b is such that no movement of the strap takes place during firing. The way this is achieved is as follows.

Instead of attaching the upper end of the strap 178 directly to the spring 160, it is attached instead to a strap tube 400 which is slidably mounted on the spring 160 for longitudinal movement therealong. The tube 400 is biased to an upper position (the position shown in FIG. 12a) by an auxiliary spring 401. The spring 401 has a much lower spring constant than the main spring 160. The upper end of the spring 401 is shown in the Figures as being held on the same mounting as that which holds the upper end of the spring 160, though it could of course have its own mounting instead. The lower end of the spring 160 is connected to a block 402. The block 402 is in turn connected to the rear end of the yoke 136.

The elements will be in the position shown in FIG. 12a when the device has been discharged. To cock the device, the user pulls downwardly on the strap 178 which slides downwardly over the spring 160 until it comes into contact with the block 402. Continued downward pulling by the user on the strap causes the block 402 to be pulled downwards against the force of the spring 160, thus cocking the device in the same way as in the case of the previously described embodiments. However, as soon as the user releases the strap it returns immediately to the position shown in FIG. 12b under the force exerted by the auxiliary spring 401. Accordingly, when the device is fired, the strap remains stationary. The block 402 moves upwardly, as does the spring 160 as it contracts. However, this does not cause any movement in the strap since the spring 160 is able to slide upwardly through the tube 400.

The construction shown in FIGS. 12a and 12b is intended to address the problem of strap movement in the context of embodiments, such as the first two embodiments, where the force of the main spring is applied constantly to the rear end of the yoke. Accordingly, further modification is required to deal with the problem of strap movement in the context of embodiments such as the one shown in FIGS. 10a to 10d and FIG. 11, where the main spring does not constantly act on the rear end of the yoke. One way of making the necessary modifications to achieve this is shown in FIGS. 13a and 13b. The reference numerals used in these Figures are those which appear in the embodiment of FIGS. 10a to 10d and FIG. 11, with additional numerals being 500 or above.

In FIGS. 13a and 13b, the strap 136 has a block 502 sliding on it, which basically corresponds in function to the block 402 in FIG. 12. The block is a loosely sliding fit on the strap. As can be seen from the rear elevation of FIG. 13b, the block 502 has a pair of strap-retaining lugs 503 which are spaced apart by a distance only slightly less than the width of the strap, so as to facilitate assembly of the block on the strap. The main spring 160 is secured at its lower end to the block 502. A strap tube 500, corresponding basically in function to the tube 400 in the embodiment of FIG. 12, extends from the front of the strap 136 and is a sliding fit around the spring 160. The strap 136 and strap tube 500 are biased upwardly by an auxiliary spring 501, corresponding in function basically to the spring 401 in the embodiment of FIG. 12.

The block 502 has a pair of openings 504 which correspond in function to the openings 301 in the embodiment of FIGS. 10a, 10d and FIG. 11. Thus, the openings 504 serve to receive rear end portions of the yoke, corresponding to the rear end portions 300 shown in connection with the embodiment of FIGS. 10a to 10d and FIG. 11.

With the modification shown in FIGS. 13a and 13b, therefore, a device is provided which both enables the metering chamber of the valve to refill immediately after discharge, and which avoids movement of the cocking strap during discharge.

It should be understood that the present disclosure is for the purpose of illustration only and includes all modifications or improvements which fall within the scope of the appended claims.

What is claimed is:

1. An inhalation device for use with an aerosol module having a body portion and a discharge stem movable with respect to the body portion from a disabling position in which it prevents discharge to an enabling position in which its permits discharge and stem biasing means for biasing the stem to the disabling position, the device comprising:
   (a) a housing,
   (b) a cradle in the housing for receiving the aerosol module, said cradle being movable relative to the housing,
   (c) a discharge nozzle member mounted in the housing for receiving the discharge stem whereby movement of the cradle relative to the housing towards the discharge nozzle member effects movement of the stem to its enabling position,
   (d) a lever mounted in the housing operable to effect said movement of the cradle relative to the housing,
   (e) spring means connected to the lever biasing the lever in a direction to enable the stem,
   (f) means for restraining movement of said lever in said enabling direction, said restraining means comprising a sear with which the lever is engageable; a latch engageable with the sear for holding the sear and thereby the lever in a position such that the stem is disabled; means for disengaging the latch from the sear such as to permit the spring to move the lever to a position to enable the discharge stem;
   (g) cocking means coupled to the lever operable to move the lever in opposition to the spring means to a position to disable the stem, and
   (h) releasable coupling means for connecting said spring means to said lever and being adapted to release, and thereby disconnect the said spring means from the said lever, when the spring means has moved the lever to the s id stem enabling position, to permit the said stem biasing means to return the stem to its disabling position.

2. A device according to claim 1, wherein the cocking means comprises a strap connected to the said spring means, and wherein the said releasable coupling means comprises means defining at least one opening in the strap and a lever portion releasably engageable in the said opening.

3. An inhalation device for use with an aerosol module having a body portion and a discharge stem movable with respect to the body portion from a disabling position in which it prevents discharge to an enabling position in which its permits discharge and stem biasing means for biasing the stem to the disabling position, the device comprising:

(a) a housing, (b) a cradle in the housing for receiving the aerosol module, said cradle being movable relative to the housing, (c) a discharge nozzle member mounted in the housing for receiving the discharge stem whereby movement of the cradle relative to the housing towards the discharge nozzle member effects movement of the stem to its enabling position, (d) a lever mounted in the housing operable to effect said movement of the cradle relative to the housing, (e) spring means connected to the lever biasing the lever in a direction to enable the stem, (f) means for restraining movement of said lever in said enabling direction, said restraining means comprising a sear with which the lever is engageable; a latch engageable with the sear for holding the sear and thereby the lever in a position such that the stem is disabled; means for disengaging the latch from the sear such as to permit the spring to move the lever to a position to enable the discharge stem;

(g) cocking means coupled to the lever operable to move the lever in opposition to the spring means to a position to disable the stem, and said cocking means comprising a strap, the device further comprising means mounting the strap for longitudinal movement with respect to the said spring means between a first, inoperative, position and a second, operative, position, and means normally urging the strap to the inoperative position, the said mounting means being so arranged that when a force is applied to the strap sufficient to overcome the force of the said urging means and move the strap to its operative position, continued application of the said force causes the lever to move to the position in which it disables the stem.

4. A device according to claim 3, for use with an aerosol module in which the discharge stem is biased by stem biasing means to its disabling position, wherein the said spring means is connected to the said lever by releasable coupling means adapted to release, and thereby disconnect the said spring means from the said lever, when the spring means has moved the lever to the said stem disabling position, to permit said stem biasing means to return the stem to its disabling position.

5. A device according to claim 4, wherein the said releasable coupling means comprises a member attached to the said spring means and mounted for longitudinal sliding movement with respect to the strap, the said member having at least one opening therein, and a lever portion releasably engageable in the said opening.

* * * * *